US010521969B2

(12) United States Patent
Kim et al.

(10) Patent No.: US 10,521,969 B2
(45) Date of Patent: Dec. 31, 2019

(54) METHOD FOR SIMULATING MANDIBULAR MOVEMENT, DEVICE FOR SAME AND RECORDING MEDIUM FOR RECORDING SAME

(71) Applicants: OSSTEMIMPLANT CO., LTD., Seoul (KR); SEOUL NATIONAL UNIVERSITY R&DB FOUNDATION, Seoul (KR); UNIVERSITY OF ULSAN FOUNDATION FOR INDUSTRY COOPERATION, Ulsan (KR)

(72) Inventors: Namkug Kim, Seoul (KR); Mooyong Park, Seoul (KR); Seongyun Lee, Seoul (KR); Byunghee Han, Seoul (KR); Il-Hyung Yang, Seongnam-si (KR); In-Sung Yeo, Seoul (KR)

(73) Assignees: OSSTEMIMPLANT CO., LTD., Seoul (KR); SEOUL NATIONAL UNIVERSITY R&DB FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 0 days.

(21) Appl. No.: 15/552,560

(22) PCT Filed: Feb. 23, 2016

(86) PCT No.: PCT/KR2016/001738
§ 371 (c)(1),
(2) Date: Aug. 22, 2017

(87) PCT Pub. No.: WO2016/137191
PCT Pub. Date: Sep. 1, 2016

(65) Prior Publication Data
US 2018/0336736 A1    Nov. 22, 2018

(30) Foreign Application Priority Data

Feb. 23, 2015  (KR) ................. 10-2015-0024940
Feb. 23, 2016  (KR) ................. 10-2016-0020997

(51) Int. Cl.
*G06T 13/00*       (2011.01)
*G06T 19/20*       (2011.01)
(Continued)

(52) U.S. Cl.
CPC .............. *G06T 19/20* (2013.01); *A61C 11/00* (2013.01); *A61C 19/045* (2013.01);
(Continued)

(58) Field of Classification Search
CPC ......... G06T 13/40; G06T 13/00; G06T 13/80; G06T 13/20; A63F 13/10
(Continued)

(56) References Cited

U.S. PATENT DOCUMENTS

2005/0197814 A1    9/2005  Aram et al.
2011/0059413 A1*   3/2011  Schutyser ............ A61B 5/1077
                                                          433/8
(Continued)

FOREIGN PATENT DOCUMENTS

JP    2004-081865    3/2004
JP    2013-192695    9/2013
(Continued)

OTHER PUBLICATIONS

International Search Report for International Application No. PCT/KR2016/001738, dated Jun. 1, 2016.

*Primary Examiner* — Gordon G Liu
(74) *Attorney, Agent, or Firm* — Kile Park Reed & Houtteman PLLC

(57) ABSTRACT

The present invention relates to method for simulating mandibular movements, device for the same and recording
(Continued)

medium for recording the same. With the method for simulating mandible movements according to the present invention, it is possible to perform the simulation directly on the medical image of the patient and thus simulate the mandibular movements more closely to the actual situation. Therefore, the inaccurate mechanical approximation of the mandibular movement with the articulator according to the conventional art is overcome. In addition, according to the present invention, it is possible to simulate mandibular movements customized to the various states of the patient and specific clinical cases.

10 Claims, 2 Drawing Sheets

(51) Int. Cl.
G06T 7/00 (2017.01)
G06T 7/207 (2017.01)
G06T 7/60 (2017.01)
A61C 19/045 (2006.01)
A61C 11/00 (2006.01)

(52) U.S. Cl.
CPC ............ *G06T 7/0012* (2013.01); *G06T 7/207* (2017.01); *G06T 7/60* (2013.01); *G06T 2207/10081* (2013.01); *G06T 2207/10116* (2013.01); *G06T 2207/30036* (2013.01); *G06T 2207/30204* (2013.01); *G06T 2219/2016* (2013.01)

(58) Field of Classification Search
USPC .......................................................... 345/473
See application file for complete search history.

(56) References Cited

U.S. PATENT DOCUMENTS

2012/0107763 A1* 5/2012 Adams .................... A61B 1/24
433/29
2012/0191421 A1 7/2012 Greenberg

FOREIGN PATENT DOCUMENTS

KR 10-2009-0105130 10/2009
KR 10-2010-0022100 2/2010

* cited by examiner

METHOD FOR SIMULATING MANDIBULAR MOVEMENT, DEVICE FOR SAME AND RECORDING MEDIUM FOR RECORDING SAME

FIELD

The present invention relates to method for simulating mandibular movements, device for the same and a recording medium for recording the same. More specifically, the present invention relates to method for simulating mandibular movements on a computer, device for the same and recording medium for recording the same.

BACKGROUND OF INVENTION

In the field of medical treatments for teeth and jaws, including various restorative treatment and orthognathic surgery with dentures, crown, etc, the process of establishing a treatment plan which is customized to be suitable for the individual condition of each patient is performed by simulating mandibular movements.

The simulation of the mandibular movements has been done with an articulator. The articulators are classified into non-adjustable articulator, semi-adjustable articulator, and full-adjustable articulator with the simulation capability. But basically, the simulation of the mandibular movement is performed with input of multiple angular values to the articulator which are main keys to the characteristic of the border movement because the mandibular movement of the articulator is done within border movement.

For accurate diagnosis and treatment, it is important to simulate the mandibular movements as closest to the actual mandibular movements, and so the research for this has continued. However, the above research, because of the limitation that the simulation of the mandibular movements is performed with the articulator, results in finding the angular values for adjusting the articulator to move as closest to the actual mandibular movements.

However, the aspects of the mandibular movements are complicated because these are done by the complex interact of the TMJ (temporomandibular joint), teeth, and masticatory muscles, etc. Whereas, since the articulator is designed by simplifying the mandibular movements with several variables for the simulation of the mandibular movements, there is an essential limitation in simulating actual the mandibular movements.

In addition, it is possible with the articulator to perform the simulation only for the border movement corresponding to the maximum movement range in which the mandible can move largest, because it is difficult to reproduce all the complex and various mandibular movements with the mechanical mechanism of the articulator. Therefore, it cannot get the information about the mandibular movements within the boundary according to the border movement, and thus cannot simulate entire the mandibular movements.

Meanwhile, since the mandibular movements are universally defined based on representative variable values, it is difficult to apply this method to the unusual patients. For example, in case of one of the jaw joints is normal while the other is abnormal, the border movement would not be symmetrically done and thus it is impossible to define the mandibular movement with several variable values input to the articulator.

As described above, if the problem caused by performing the simulation with the articulator can be solved fundamentally, it would be expected that the range of applicable clinical cases is widened and simulations in conformity with actual situation are performed more in conformity with the actual thing.

Technical Challenge

The present invention is proposed in order to solve the problems of the conventional art in which there are limitations with articulator not to simulate the precise mandibular movements and not to apply various clinical cases. An object of the present invention is to provide the method for simulating mandibular movements capable of simulating mandibular movements for the various types of the patients and unusual cases and improving its accuracy, the device for the same and the recording medium for recording the same.

The Solution of Invention

In order to achieve the above object, in accordance with one aspect of the present invention, method for simulating mandibular movements, comprises: storing a mandibular movement model that defines relationship between anatomical characteristics and characteristics of mandibular movements; extracting the anatomical characteristics related to the characteristics of mandibular movements from a medical image of patient; estimating the mandibular movements of the patient from the extracted anatomical characteristics and the mandibular movement model: and performing a simulation by changing a mandibular position in the medical image of the patient according to the estimated mandibular movements.

Also, in order to achieve the above object, in accordance with another aspect of the present invention, a computer-readable recording medium has a program to execute the method for simulating mandibular movements.

Also, in order to achieve another the object, in accordance with another aspect of the present invention, a device for simulating mandibular movements, comprises: a mandibular movement model storage unit storing a mandibular movement model that defines relationship between anatomical characteristics and characteristics of mandibular movements; a characteristic extraction unit for extracting anatomical characteristics related to the characteristics of mandibular movements from a medical image of the patient; a mandibular movement estimation unit for estimating the mandibular movements of the patient from extracted the anatomical characteristics and the mandibular movement model; and a simulation unit for performing a simulation by changing a mandibular position in the medical image of the patient according to the estimated mandibular movements.

In addition, the mandibular movement model storage unit may store the mandibular movement model including at least one of submodels, each corresponding to each of opening and closing movement, forward movement, rearward movement, lateral movement, and border movement. And, the simulation unit may store simulation scenarios according to at least one of a simulation execution purpose, a treatment type, a treatment position, a state of the patient, or a movement type and perform the simulation based on the selected scenario among the simulation scenarios.

Also, the device for simulating mandibular movements further comprises a motion tracking unit for tracking position of a marker fixed on the mandible of the patient and detecting the movements of the mandible, wherein the motion tracking unit is activated when the mandibular movement model applicable to the medical image does not exist, wherein the simulation unit performs the simulation by reflecting the movement of mandible according to the motion tracking unit to the medical image.

Also, the device for simulating mandibular movements further comprises a display unit for providing a simulation video in which the mandibular position of the medical image is continuously changed according to a predetermined simulation scenario.

The Effect of Invention

As stated above, according to the present invention, the approximation of the movement with the articulator is excluded, and thus the mandibular movements can be simulated more closely to the actual situation.

Also, according to the present invention, it is possible to simulate mandibular movements customized to the various states of the patient and specific clinical cases.

DETAILED DESCRIPTION OF EXEMPLARY EMBODIMENTS

Figure 1:
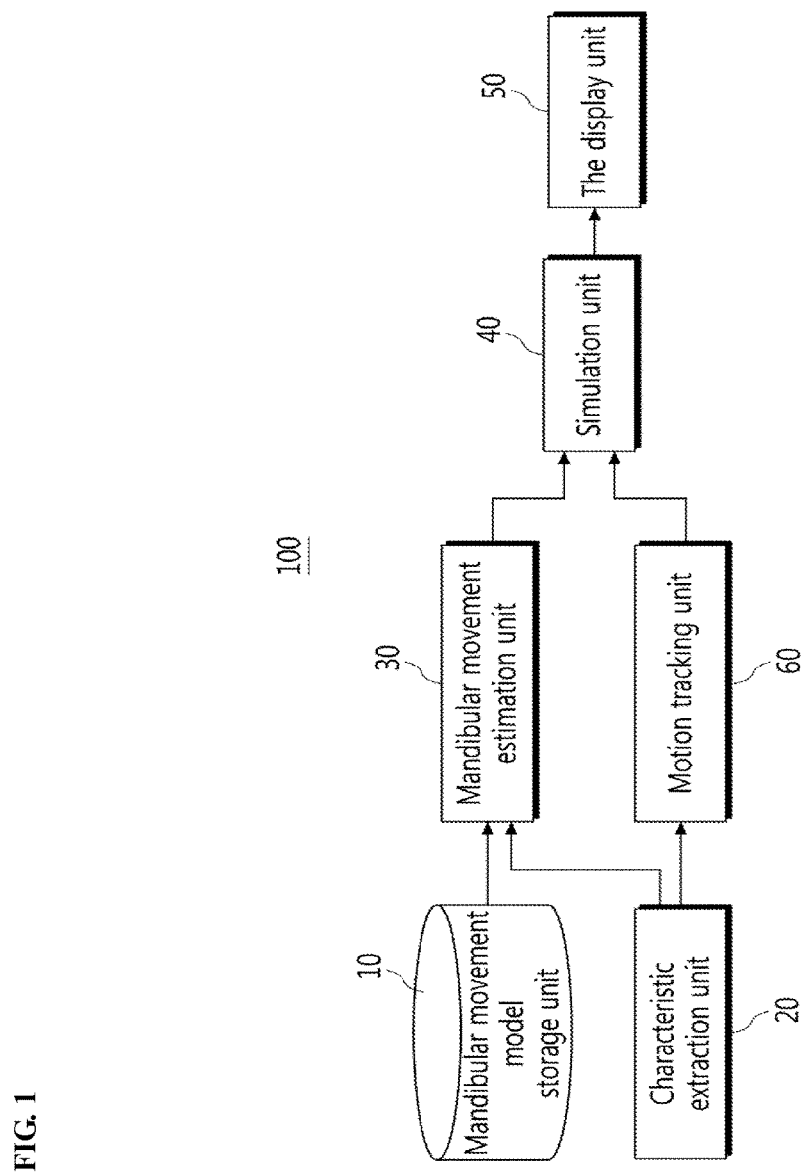
FIG. 1 is a block diagram of the device for simulating mandibular movements according to an embodiment of the present invention.

Hereinafter, with reference to the accompanying drawings, preferred embodiments of the present invention will be described in detail. However, the explanation on the known functions and configurations that may obscure the subject matter of the present invention from the detailed description of the following description and from the accompanying drawings will be omitted. In addition, the same components throughout the drawings are referred to by the same reference numerals as possible which is to be noted.

The terms used in this specification and claims is not to be construed as limited to dictionary meanings, but can be defined and interpreted based on the meanings and concepts corresponding to technical aspects of the present invention in the principle that inventors define the terms appropriate to the concept of a term to describe his own invention in the best way. Therefore, the present embodiment and the configuration shown in the drawings and described in the specification is merely nothing but a preferable embodiment of the present invention, as not intended to represent all the technical concept of the present invention, so that it should be understood that many equivalents and varied modified embodiments of the present invention that can be made in the present application point.

Device for simulating mandibular movements according to the present invention performs the simulation of mandibular movements necessary for establishing various treatment plans for teeth and jaws including restorative treatment by dentures, crown, or orthognathic surgery, etc.

FIG. 1 is a block diagram of the device for simulating mandibular movements according to an embodiment of the present invention. Referring to FIG. 1, the device for simulating mandibular movements 100 according to the present invention comprises mandibular movement model storage unit 10, characteristic extraction unit 20, mandibular movement estimation unit 30, simulation unit 40, display unit 50, motion tracking unit 60.

Mandibular movement model storage unit 10 stores a mandibular movement model that defines the relationship between the anatomical characteristics and the characteristics of mandibular movements determined by the anatomical characteristics. The mandibular movement model can be defined as a function of mandibular movements according to anatomical characteristics. Here, the anatomical characteristics is related to mandibular movements that can be observed through various medical images including CT (Computed Tomography) images. For example, it comprises various anatomical factors including shape, size, condition, angle, inter-structure distance, length, and the like of structures jaw joints, teeth, bones, and neuromuscular tissues, etc that appear to be associated with mandibular movements.

The mandibular movement model includes information on movement distance, movement direction, movement angle, and movement path of the mandible on a two-dimensional or three-dimensional plane of a multi-plane, such as a horizontal plane, sagittal plane, frontal plane, and can be implemented as a stochastic model as well as a deterministic model.

Meanwhile, the mandibular movement model can be divided into a plurality of submodels corresponding to the types of mandibular movements. For example, mandibular movements can be divided according to the movement characteristics into rotational movements that the condyles rotate around the limited axes and sliding movements that the condyle shifts, and can be divided according to the functions of movements into the opening and closing movement that the mandible opens and closes, the forward movement that the mandible moves forward, the rearward movement that the mandible moves the rear, and the lateral movement that the mandible moves to the left and right. In short, the mandibular movement model can be constructed with each submodels corresponding to each types of the mandibular movements.

Characteristic extraction unit 20 analyzes the medical image of the patient acquired by imaging equipment to extract anatomical characteristics. The extracted anatomical characteristic is an anatomical characteristic applied to the mandibular movement model and means specific information such as position of anatomical structure, size, shape, distance between structures, state, angle information, etc. Meanwhile, the medical image would be CT image, X-ray image, or two-dimensional or three-dimensional head and neck images of the maxilla and mandible to extract anatomical characteristics and not be limited to a specific kind of image.

In order to extract the anatomical characteristics, the characteristic extraction unit 20 includes various image processing algorithms for recognizing and processing the related anatomical structures in the medical image.

The mandibular movement estimation unit 30 applies the anatomical characteristics extracted from the medical image to the mandibular movement model to estimate the mandibular movement of the patient. The mandibular movement estimating unit 30 may store various interpolation algorithms for interpolating the mandibular movement data on the two-dimensional and/or three-dimensional images, and estimate the mandibular movements using the interpolation algorithm.

The simulation unit 40 performs simulation with changing mandibular position in the medical image of the patient based on the mandibular movements estimated by the mandibular movement estimation unit 30. The simulation unit 40 separates the mandible from the medical image and performs simulation based on the medical image with continuously changing the mandibular position relative to the maxilla position according to the estimated mandibular movements. Here, the estimated mandibular movements mean, for example, the estimated movement distance of mandible, movement direction, movement angle, movement path, etc.

Meanwhile, the simulation unit 40 may prepare simulation scenarios, each of which corresponds to each of various situations and perform the simulation according to the suitable one of the scenarios. For example, the scenario may vary according to whether the simulations performed are used in denture design or orthognathic surgery. For the denture design, the scenario may vary according to the partial denture or the entire denture for the edentulous since the necessary motion of the mandibular movement for each of them would be different.

As described above, the simulation unit 40 can be implemented to store simulation scenarios that specify specific motions required in various situation, select a scenario suitable for the situation from the stored scenarios, and perform the simulation for the mandibular movements according to the selected one. Here, the various situation comprises the various states of the patient such as simulation purpose, a treatment type, a treatment position, the state of edentulous jaw or dentulous jaw, and a movement type The display unit 50 displays a moving picture of the medical image in which the mandibular position is continuously changed relatively to the position of the maxilla in the simulation of mandibular movements based on the medical image of the patient. At this time, the display unit 50 may provide the moving picture in various views including a three-dimensional image, a two-dimensional image of sagittal plane, horizontal plane, coronal plane, etc. to observe the simulation.

As described above, when simulating the mandibular movements, the device for simulating the mandibular movements 100 according to the embodiment of the present invention simulates the precise mandibular movements of the patient based on the medical image without a mechanical mechanism with conventional articulators. Meanwhile, since the simulation is performed in the medical image based on the mandibular movement model, it is not necessary to record the movement of the patient individually, which is convenient.

However, as a result of analyzing the medical image, there may be cases that do not accord with the mandibular movement model. For example, the cases of the unusual patient such as the deformed mandible patient and deficient mandible patient may not be applied to the model prepared in advance.

In order to prepare for such unusual cases, the device for simulating mandibular movements 100 according to the embodiment of the present invention further includes a motion tracking unit 60. The motion tracking unit 60 is activated in the mentioned cases that there is no applicable mandibular movement model. That is, the motion tracking unit 60 is activated automatically according to the image analysis result from the characteristic extraction unit 20 or activated by user command through user interface.

A marker is fixed to the mandible of the patient and the various mandibular movements of the patient are guided and scanned. The motion tracking unit 60 tracks the movement of the marker moving along with the mandible from the scan data acquired by scanning the mouse of the patient. The marker is fixed to at least one part of the mandible and is exposed to be tracked in facial scanning. For example, for the dentulous patient the marker can be fixed to the mandible and exposed to the outside, and for the edentulous patient the marker can be connected to the fixed member implanted on the mandibular gum and exposed to the outside.

The motion tracking unit 60 acquires a medical image and a facial scan image of the patient taken of a predetermined reference posture of mandible with the marker fixed to the mandible and matches the medical image and the facial scan image based on the marker position to get the initial marker position and the initial posture of the mandible Then, the motion tracking unit 60 compares the initial marker position with the tracked position of the marker in the acquired facial scan image for the guided mandibular movements such as lateral movement, opening and closing movement, forward and rearward movement, etc, to get the mandibular movements in the medical image. At this time, the motion tracking unit 60 can reflect synthetically the changes of the facial line and the marker position caused by the mandibular movements to get the mandibular movements.

The simulation unit 40 performs the simulation with changing the mandibular position in the medical image according to the mandibular movements detected by the movement tracking unit 60 in the above-described manner.

Simulation results of the simulation unit 40 are taken into consideration together with the anatomical structure acquired from the medical image in establishing a treatment plan such as the angle, shape, and position of the crown to be restored with.

Figure 2:
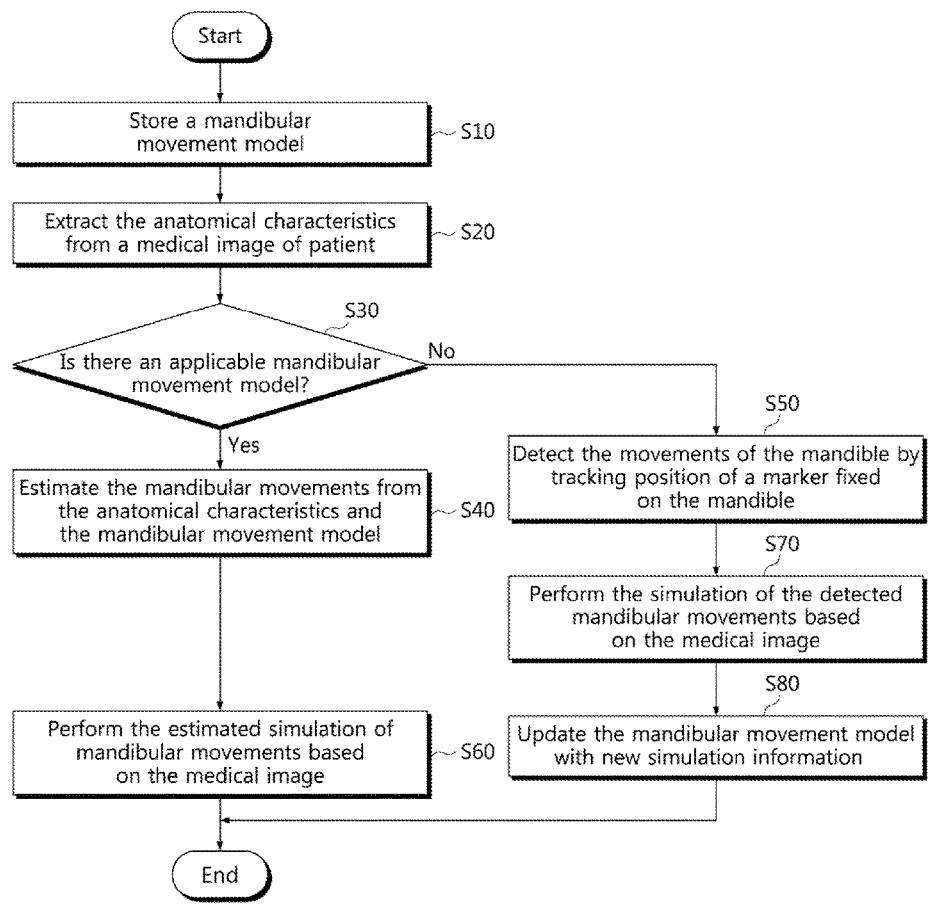
FIG. 2 is a flowchart of the method for simulating mandibular movements according to an embodiment of the present invention.

FIG. 2 is a flowchart of the method for simulating mandibular movements according to an embodiment of the present invention. Hereinafter, referring to FIG. 2, the organic operation of the above-described configuration of the device for simulating mandibular movements 100 will be described.

First, a database is provided in which a mandibular movement model defining relationship between anatomical characteristics and the characteristics of mandibular movements is stored (S10). The mandibular movement model may be subdivided according to the movement type and anatomical characteristics. For reference, the mandibular movement model is modeled on the basis of various experimental data acquired by tracking the movement of the markers in the facial scan image for various mandibular movements guided to the patient with the marker fixed to the mandible as the motion tracking unit 60 does.

The mandibular movement model is used to simulate the mandibular movements of the patient, as described below. First, the anatomical characteristics are extracted from the medical image of the patient(S20). Here, the anatomical characteristics correspond to the variables of the mandibular movement model and include various anatomical factors related to mandibular movements, such as the shape of the structures of the jaw joint, teeth, bones, neuromuscular tissues, etc, angle, size, distance between structures, length and the like.

Subsequently, the extracted anatomical characteristic is applied to the mandibular movement model and then the mandibular movements of the patient is estimated (S30, S40). In this step, when the mandibular movement model is multiple or divided into a plurality of submodels, an appropriate model can be selected based on predetermined model setting criteria according to the extracted anatomical characteristics On the other hand, when there is no mandibular movement model which is suitable for the extracted anatomical characteristics of specific cases such as deficient mandible, deformed mandible, since it is impossible to estimate the mandibular movements with the mandibular movement model, detecting the mandibular movements by tracking the marker attached to the mandible of the patient is performed (S50).

The simulation is performed with changing the mandibular position of the patient in the medical image according to the mandibular movement model or the mandibular movements detected from the tracked position of the marker attached to the mandible (S60, S70). The simulation is performed according to a user's input or a pre-stored simulation scenario, and the process of the simulation can be provided to the user as a moving picture in which the mandibular position of the medical image is continuously changed relatively to the maxilla position. At this time, tools for additional functions such as angle adjustment, view selection, and screen enlargement/reduction of the provided screen may be provided to improve the usability of the user.

Meanwhile, since the mandibular movements detected by tracking the marker attached to the mandible and the simulation information of the mandibular movements using the same are not present in the pre-stored mandibular movement model, it is possible to update the model with the mandibular movements and the simulation information (S80). In addition, it is possible to implement a more accurate mandibular movement estimation algorithm by continuously updating the mandibular movement model with new data collected in different paths.

The simulation of the mandibular movements through the steps described above can be used to establish the treatment plan such as crown restoration position, shape, and restoration angle determination.

As described above, according to the device for simulating mandibular movements 100 and the method according to the present invention, it is possible to simulate the mandibular movements more closely to the actual situation by excluding the approximation of the movement with an analog or digital articulator, and it is possible to simulate mandibular movements customized to the various states of the patient and a specific clinical cases, so that more successful treatment plan can be established than with the conventional articulator.

Meanwhile, the method for simulating mandibular movements according to the embodiment of the present invention may be implemented as a program that can be executed in a computer, and may be implemented by using various recording media such as a magnetic storage medium, an optical reading medium, and a digital storage medium, etc.

Implementations of the various techniques described herein area digital electronic circuitry, or computer hardware, firmware, software, or may be implemented in a combination of them. Implementations can be implemented by a data processing device, for example, a programmable processor, a computer, or for processing by the operation of a plurality of computers, or to control the operation, the computer program product, i.e. the information carrier, for example, machine-readable apparatus (computer readable medium) or a radio signal. The computer program as stated above can be recorded in a programming language of any type, including a substituted or interpret compiled language, as a stand-alone program or as a module, component, subroutine, or in the computing environment, it may be deployed in any form, including as appropriate, including the use of other units. Computer program can be distributed across one or more computer or a number of sites to be processed on multiple computers at one site, and can be connected by a communication network.

Processors suitable for the processing of the computer program comprise as an example, includes both general and special purpose microprocessors, and more than one processors of any kind of digital computer. Generally, a processor may receive commands or data from read-only memory or random-access memory or both. The computer can include more than one memory device saving at least one processor and commands and data which executes commands. For example, it includes magnetism, magnetic-optical disks, or optical disks, or transmitting this data or combining both, or it can receive or transmit data or combine both. Information carriers appropriate for specifying computer program commands or data as an example, semiconductor memory device, for example, includes hard disks, floppy disks, and magnetic tape, such as magnetic media, CD-ROM (Compact Disk Read Only Memory), DVD (Digital Video disk) and the like optical recording media, floptical disk, such as magneto-optical media, ROM (Read Only Memory), RAM (Random Access memory), comprises a flash memory, EPROM (Erasable Programmable ROM), EEPROM (Electrically Erasable Programmable ROM) etc. Processor and memory can be added or included by special purpose logic circuitry.

The present description herein includes details a number of specific implementations, but it cannot be understood as limited for any invention or scope for patent claims, rather to be understand as explanation about featuring specific implementation of specific invention. The specific features of the present description in context of each implementation herein can be implemented in combination in a single embodiment. Conversely, it also can be implemented in a plurality of embodiments with different features, any suitable sub-combination or separately described in the context of a single embodiment. Furthermore, the features can be combined as specific combinations or described as claimed in early, but one or more features from claimed combinations can be excluded from the combination in some cases, the claimed combination can be changed as sub-combination or its modifications.

Likewise, although it describes operations as particular order, it cannot be understood that performing those operations as the specific or sequential order described to achieve desired results or being performed for all described operations. In certain case, multi-tasking and parallel processing can be advantageous. In addition, separation of various system components in the embodiments described above should not be understood to require in any embodiment such a separation, the described program components and systems are generally integrated together in a single software product or be packaged into multiple software products number that should be understood.

On the other hand, the embodiments of the invention disclosed in the specification and drawings are not presented merely a specific example for clarity and are not intended to limit the scope of the invention. It addition to the embodiments disclosed herein another modification based on the technical ideas of the invention are possible embodiments, it will be apparent to those of ordinary skill in the art.

What is claimed is:
1. A method for simulating mandibular movements, comprising:
   storing a mandibular movement model that defines a relationship between anatomical characteristics and characteristics of mandibular movements and is defined as a function of mandibular movements according to the anatomical characteristics;

extracting the anatomical characteristics which correspond to variables of the mandibular movement model and are related to the characteristics of mandibular movements from a medical image of patient;

estimating the mandibular movements of the patient from the extracted anatomical characteristics and the mandibular movement models; and separating the mandible from the medical image of the patient and performing a simulation by continuously changing a position of the separated mandible relative to the maxilla by changing a position of the mandible in the medical image of the patient according to the estimated mandibular movements.

2. A computer-readable recording medium having a program to execute the method for simulating mandibular movements according to claim 1.

3. The method according to claim 1, wherein the mandibular movement model includes at least one of submodels, each corresponding to each of opening and closing movement, forward movement, rearward movement, lateral movement, and border movement.

4. A computer-readable recording medium having a program to execute the method for simulating mandibular movements according to claim 3.

5. The method according to claim 1, wherein the performing the simulation comprises storing simulation scenarios according to at least one of a simulation purpose, a treatment type, a treatment position, a state of the patient, or a movement type, and performing the simulation based on the selected scenario among the simulation scenarios.

6. The method for according to claim 5, further comprising providing a simulation video in which the mandibular position of the medical image is continuously changed according to a predetermined simulation scenario.

7. A computer-readable recording medium having a program to execute the method for simulating mandibular movements according to claim 6.

8. A computer-readable recording medium having a program to execute the method for simulating mandibular movements according to claim 5.

9. The method according to claim 1, wherein the estimating the mandibular movements of the patient comprises tracking position of a marker fixed on the mandible of the patient and detecting the movements of the mandible when the mandibular movement model applicable to the medical image does not exist, and wherein the performing the simulation performs the simulation by reflecting the movements of the mandible according to the motion tracking unit to the medical image.

10. A computer-readable recording medium having a program to execute the method for simulating mandibular movements according to claim 9.

* * * * *